United States Patent [19]

Sahley

[11] Patent Number: 5,051,258

[45] Date of Patent: Sep. 24, 1991

[54] DIETARY SUPPLEMENT FOR CHILDREN

[75] Inventor: Billie J. Sahley, San Antonio, Tex.

[73] Assignee: Natrol, Inc., Chatsworth, Calif.

[21] Appl. No.: 497,900

[22] Filed: Mar. 23, 1990

Related U.S. Application Data

[63] Continuation-in-part of Ser. No. 421,016, Oct. 13, 1989, Pat. No. 4,980,168.

[51] Int. Cl.$^5$ .................................................. A61K 9/48
[52] U.S. Cl. .................................. 424/439; 424/195.1; 424/451; 514/904; 514/905; 426/72; 426/74
[58] Field of Search ................ 424/439, 451; 514/904, 514/905; 426/72, 74

[56] References Cited

U.S. PATENT DOCUMENTS 4,980,168 10/1989 Sahley .................................. 424/439

Primary Examiner—Thurman K. Page
Assistant Examiner—James M. Spear
Attorney, Agent, or Firm—Ashen Martin Seldon Lippman & Scillieri

[57] ABSTRACT

A dietary supplement is provided for children, consisting essentially of GABA (gamma-aminobutyric acid), Passion Flow Extract, L-taurine, and vitamin B6.

3 Claims, No Drawings

DIETARY SUPPLEMENT FOR CHILDREN

RELATED APPLICATIONS

This application is a continuation-in-part application of my application Ser. No. 07/421,016, filed on Oct. 13, 1989, now U.S. Pat. No. 4,980,168, and entitled "Dietary Supplement For Children".

This application is also related to my copending application Ser. No. 07/421,138, filed and on Oct. 13, 1989, and entitled "Dietary Supplement For Adults". The latter application discloses another dietary mixture of amino acids and vitamin B6, especially designed for adults.

TECHNICAL FIELD

This invention is concerned with a special blend of amino acids and vitamin B6 which has been designed to help a child's needs for a normally active lifestyle. The blend may be supplemented with other amino acids, vitamins, and/or minerals.

BACKGROUND ART

Dietary imbalance is known to cause physiological disorders in children. Among these disorders are hyperactivity, hyperkinesis, and learning disabilities. In 1988, there were approximately one million children taking Ritalin for hyperactivity. Ritalin is a potent drug that is available only by prescription. Of the five classes of controlled substances set out by the United States Drug Enforcement Administration based on potential abuse, Ritalin is listed in Schedule II along with morphine and opium. Obviously, in those cases where a dietary regimen can control or relieve the symptoms and Ritalin treatment can be discontinued or reduced, such a change is in the best interest of the child.

Members of the Academy of Orthomolecular Medicine and other prominent researchers have shown that hyperactivity and certain learning disabilities can be treated by orthomolecular therapy. Orthomolecular therapy is the treatment of a condition in a patient by varying the concentration of substances normally present in the human bodies. These substances, which are referred to as "the right molecules", are vitamins, minerals, trace elements, hormones, amino acids, and enzymes. Regulation of the concentration of these molecules in the body helps in the achievement and preservation of optimum health and the prevention and treatment of disease.

If the level of any of "the right molecules" in a child's system is low, it can produce a disturbed biochemical homeostasis, which, in turn, results in brain malfunctions. This, in turn, can cause a child to be hyperactive. Behavior symptoms of hyperactivity may be aggressive or passive. Among the aggressive symptoms are angry outbursts, restlessness, stealing, inability to concentrate, compulsive aggression, lying, etc. The passive symptoms include anxiousness, reasoning difficulties, shyness, insecurity, sleep problems, etc.

Various dietary supplements have been used in the past with children who have shown symptoms of hyperactivity. One of the best of these supplements is sold by NATROL, INC., Chatsworth, Calif. Six capsules of the product contain:

|  |  | USRDA* |
|---|---|---|
| Niacinamide | 200 mg | 1000% |
| Calcium | 200 mg | 20% |
| Vitamin D | 100 I.U. | 25% |
| Vitamin B6 | 100 mg | 5000% |
| Magnesium | 100 mg | 25% |
| Zinc | 10 mg | 66% |
| GABA | 500 mg |  |
| L-Tryptophan | 500 mg |  |
| L-Taurine | 500 mg |  |
| Inositol | 200 mg |  |

*Percent U.S. Recommended Daily Allowance

The recommended dosage of this formulation for children between the ages of four and fifteen is four to six capsules per day.

DISCLOSURE OF INVENTION

A dietary supplement is provided for children, consisting essentially of GABA (gamma-aminobutyric acid), L-tryptophan or Passion Flower Extract, L-taurine, and vitamin B6.

BEST MODES FOR CARRYING OUT THE INVENTION

I have discovered improved nutritional formulas. The formulations consists essentially of the following, parts by wt:

| A. | GABA | from about 34 to about 40 |
|---|---|---|
|  | L-Tryptophan | from about 34 to about 40 |
|  | L-Taurine | from about 20 to about 25 |
|  | Vitamin B6 | from about 2 to about 3. |
| or |  |  |
| B. | GABA | from about 40 to about 45 |
|  | Passion Flower Extract | from about 25 to about 30 |
|  | L-Taurine | from about 25 to about 30 |
|  | Vitamin B6 | from about 2.5 to about 3. |

Other amino acids, vitamins, and minerals may be included. For instance, glycine, vitamin C (as Ester C), calcium, and magnesium are valuable additons. ( ESTER C is a registered trademark of Inter-Cal Corp.) This form is superior to regular ascorbic acid and delivers four times the normal amount to the system.

The new compositions are preferably put into capsules, along with other "right molecules", so that six capsules, which would be the recommended daily dose for a child at least four years of age or an adult, will contain the following:

|  |  |  | USRDA* |
|---|---|---|---|
| A. | GABA | 720 to 880 mg |  |
|  | L-Tryptophan | 720 to 880 mg |  |
|  | Glycine | 450 to 550 mg |  |
|  | L-Taurine | 450 to 550 mg |  |
|  | Vitamin C (as Ester C) | 55 to 65 mg | 90 to 110% |
|  | Calcium | 90 to 110 mg | approx. 10% |
|  | Vitamin B6 | 45 to 55 mg | 2250 to 2750% |
|  | Magnesium | 45 to 55 mg | 10 to 14%. |
| or |  |  |  |
| B. | GABA | 720 to 880 mg |  |
|  | Passion Flower Extract | 450 to 550 mg |  |
|  | Glycine | 720 to 880 mg |  |
|  | L-Taurine | 450 to 550 mg |  |
|  | Vitamin C (as Ester C) | 55 to 65 mg | 90 to 110% |

-continued

|  | USRDA* |
|---|---|
| Calcium | 90 to 110 mg | approx. 10% |
| Vitamin B6 | 45 to 55 mg | 2250 to 2750% |
| Magnesium | 45 to 55 mg | 10 to 14%. |

*Percent U.S. Recommended Daily Allowance for adults and children four or more years of age.

Preferred formulations contain the following in six capsules:

|  |  |  | USRDA* |
|---|---|---|---|
| A. | GABA | 800 mg |  |
|  | L-Tryptophan | 800 mg |  |
|  | Glycine | 500 mg |  |
|  | L-Taurine | 500 mg |  |
|  | Vitamin C | 60 mg | 100% |
|  | (as Ester C) |  |  |
|  | Calcium | 100 mg | 10% |
|  | Vitamin B6 | 50 mg | 2500% |
|  | Magnesium | 50 mg | 12.5%, |
| or |  |  |  |
| B. | GABA | 800 mg |  |
|  | Passion Flower Extract | 500 mg |  |
|  | Glycine | 800 mg |  |
|  | L-Taurine | 500 mg |  |
|  | Vitamin C | 60 mg | 100% |
|  | (as Ester C) |  |  |
|  | Calcium | 100 mg | 10% |
|  | Vitamin B6 | 50 mg | 2500% |
|  | Magnesium | 50 mg | 12.5%. |

GABA is gamma-aminobutyric acid. According to a 1982 publication in *Life Extension* by Sandy Shaw and Durk Pearson, it mimics the tranquilizing effect of Valium and Librium but without the sedation associated with those drugs. A report in the Aug. 14, 1982 issue of *Lancet* stated that GABA is a major inhibitory transmitter in the mammalian central nervous system. GABA works well with other amino acids in hyperactive children.

L-tryptophan is necessary to maintain protein balance in the body. It is needed in the formation of serotonin, a neurotransmitter. Low tryptophan and serotonin have been noted in many hyperactive children.

Passion Flower Extract is a dry hydroalcoholic extract from *Passiflora incarnata* concentrated six times. The extract is standardized to contain 3.5% naturally occurring isovitexin. It is very effective as a sedative with a pleasant taste and surprisingly gentle. Both dried leaves and stems have been used to induce sleep, and it has been used in Italy to calm hyperactive children.

Normal development and health of the central nervous system requires taurine. It has been shown to be important in the control of hyperactive or hyperkinetic movements.

Vitamin B6 (pyridoxine) is the most important vitamin for amino acid metabolism because it is the cofactor for the enzymes called transaminase, which metabolize amino acids.

Glycine seems to be an important factor in the treatment of psychiatric disorders. Some manic-depressive patients have shown remission when treated with glycine even though they had previously been unresponsive to drugs.

In the treatment of hyperactivity, vitamin C is important. A study in 1987 showed that Ester C is neutral and is four times more bioavailable than ordinary vitamin C. Most children using Ester C have shown excellent response.

Magnesium deficiency is common in children with hyperactivity. Magnesium has been used as a nervous system sedative, and sometimes has an immediate calming effect when added to the diet of a hyperactive person. Magnesium oxide is a preferred form.

Children who have low calcium levels may be irritable, angry, and inattentive as well as suffer from disturbed sleep. Upon administration of calcium, edginess disappears.

The compositions and capsules of this invention may include pharmaceutically acceptable inerts, such as calcium carbonate and magnesium stearate.

When hyperactive children who are four years or older are provided a dietary supplement of approximately six capsules a day containing the above formulation in the indicated levels, they show at least a 40 to 50% improvement in behavior and learning ability.

I claim:

1. A dietary composition consisting essentially of the following parts, by weight:

| GABA | from about 40 to about 45, |
|---|---|
| Passion Flower Extract | from about 25 to about 30, |
| L-Taurine | from about 25 to about 30, |
| Vitamin B6 | from about 2.5 to about 3. |

2. A dietary composition in capsule form such that six capsules contain:

| GABA | 720 to 880 mg, |
|---|---|
| Passion Flower Extract | 450 to 550 mg, |
| Glycine | 720 to 880 mg, |
| L-Taurine | 450 to 550 mg, |
| Vitamin C | 55 to 65 mg |
| Calcium | 90 to 110 mg |
| Vitamin B6 | 45 to 55 mg |
| Magnesium | 45 to 55 mg |

3. A dietary composition in capsule form such that six capsules contain:

| GABA | 800 mg |
|---|---|
| Passion Flower Extract | 500 mg |
| Glycine | 800 mg |
| L-Taurine | 500 mg |
| Vitamin C | 60 mg |
| Calcium | 100 mg |
| Vitamin B6 | 50 mg |
| Magnesium | 50 mg |

* * * * *